United States Patent
Snyder et al.

(10) Patent No.: US 7,001,738 B2
(45) Date of Patent: Feb. 21, 2006

(54) METHOD FOR ASSAYING PROTEIN NITROSYLATION

(75) Inventors: Solomon H. Snyder, Baltimore, MD (US); Samie R. Jaffrey, New York, NY (US); Christopher D. Ferris, Franklin, TN (US); Hediye Erdjument-Bromage, New York, NY (US); Paul Tempst, New York, NY (US)

(73) Assignees: The Johns Hopkins University, Baltimore, MD (US); Memorial Sloan-Kettering Cancer Center, New York, NY (US)

( * ) Notice: Subject to any disclaimer, the term of this patent is extended or adjusted under 35 U.S.C. 154(b) by 38 days.

(21) Appl. No.: 10/927,140

(22) Filed: Aug. 27, 2004

(65) Prior Publication Data

US 2005/0026227 A1 Feb. 3, 2005

Related U.S. Application Data

(62) Division of application No. 09/984,345, filed on Oct. 29, 2001, now Pat. No. 6,806,057.

(60) Provisional application No. 60/244,097, filed on Oct. 27, 2000.

(51) Int. Cl.
*G01N 33/53* (2006.01)

(52) U.S. Cl. .................. 435/7.5; 435/7.1; 435/7.21; 435/26; 435/188; 435/7.72; 435/7.9; 436/518; 436/173; 514/562; 530/402; 530/408; 530/409

(58) Field of Classification Search ............... 435/7.1, 435/7.5, 7.72, 7.9; 436/518, 173; 514/562; 530/402
See application file for complete search history.

(56) References Cited

U.S. PATENT DOCUMENTS

| 4,281,061 A | * | 7/1981 | Zuk et al. ................. 435/7.9 |
| 4,931,392 A | | 6/1990 | Rehner et al. |
| 6,310,270 B1 | | 10/2001 | Huang et al. |
| 2002/0037532 A1 | * | 3/2002 | Regnier et al. ........... 435/7.1 |

FOREIGN PATENT DOCUMENTS

WO    WO 00 20556 A    4/2000

OTHER PUBLICATIONS

Jaffrey et al., "Protein S-nitrosylation: a physiological for neutronal nitric oxide", *Nature Cell Biology*, (Feb. 2001), pp. 193-197, vol. 3.

Jaffrey et al., "The Biotin Switch Method for the Detection of S-Nitrosylated Proteins", *Sciences stke www.stke.org/cgi/content/full/OC_sigtrans:2001/86/pl1*. (Jun. 12, 2001), pp. 1-9.

Mannick et al., "Fas-induced caspase denitrosylation", *Science*, (Apr. 23, 1993), pp. 651-654, vol. 284, No. 5414.

(Continued)

*Primary Examiner*—Long Le
*Assistant Examiner*—Deborah A. Davis
(74) *Attorney, Agent, or Firm*—Banner & Witcoff, Ltd.

(57) ABSTRACT

Many of the effects of nitric oxide are mediated by the direct modification of cysteine residues resulting in an adduct called a nitrosothiol. A method to detect proteins which contain nitrosothiols involves several steps. Nitrosylated cysteines are converted to tagged cysteines. Tagged proteins can then be detected, for example, by immunoblotting and/or can be purified by affinity chromatography. The method is applicable to the detection of S-nitrosylated proteins in cell lysates following in vitro S-nitrosylation, as well as to the detection of endogenous S-nitrosothiols in selected protein substrates.

36 Claims, 4 Drawing Sheets

OTHER PUBLICATIONS

Nohammer et al., "Mercurochrom can be used for the histochemical demonstration and microphotometric quantitation of both protein thiols and protein (mixed) disulfides", 1997, *Histochem Cell Biology*, vol. 107, pp 383-390.

Ravinder et al., "Mechanism of Nitric Oxide Release from S-Nitrosothiols", 1996, *The Journal of Biological Chemistry*, vol. 271, No. 31, Issue of 8/2, pp 18496-18603.

Rossi et al., "A method to study kinetics of transnitrosation with nitrosoglutahione: Reactions wit hemoglobin and other thiols", *Analytical Biochemistry*, (Dec. 15, 1997), pp. 215-220, vol. 254, No. 2.

Singh et al., "Mechanism of nitric oxide release from S-nitrosothiols", *Journal of Biological Chemistry*, (1996), pp. 18596-18603, vol. 271, No. 31.

Wu et al., "Kinetics of coupling reactions that generate monothiophosphate disulfides: Implications for modification of RNAs", *Bioconjugate Chemistry*, (Nov. 2001), pp. 842-844, vol. 12, No. 6.

Xian et al., "Inhibition of Papain by S-Nitrosothiols", Jul. 7, 2000, *The Journal of Biological Chemistry*, vol. 275, No. 27, pp 20467-20473.

* cited by examiner

METHOD FOR ASSAYING PROTEIN NITROSYLATION

This application is a division of Ser. No. 09/984,345 filed Oct. 29, 2001, now U.S. Pat. No. 6,806,057 which claims the benefit of provisional application Ser. No. 60/244,097 filed Oct. 27, 2000.

This invention was made using funds from the U.S. government under grants MH18501, DA00266, and DA00074 from the National Institutes of Health. The government therefore retains certain rights to the invention.

BACKGROUND OF THE INVENTION

1. Field of the Invention

The invention relates to the field of post-translational modifications of protein structure. In particular, it relates to the field of assays for one such modification that is involved in the modulation of protein function.

2. Background of the Prior Art

NO donors and endogenously produced NO exert pleiotropic effects including smooth muscle relaxation, cellular proliferation, apoptosis, neurotransmitter release, neurotoxicity, and differentiation. In mediating vasorelaxation, NO stimulates cGMP formation by binding to heme at the active site of soluble guanylyl cyclase which leads to a conformational alteration that augments enzyme activity[1]. NO also can interact with cysteines to form nitrosothiol adducts[2-4], altering the activity of proteins including H-ras[5], the olfactory cyclic nucleotide-gated channel[6], and glyceraldehyde-3-phosphate dehydrogenase (GAPDH)[7]. Nitrosothiols are exceptionally labile due to their reactivity with intracellular reducing agents such as ascorbic acid and glutathione[8], as well as reduced metal ions, especially $Cu(I)$[9], with tissue half-lives of seconds to a few minutes[8].

The reversible regulation of protein function by S-hitrosylation has led to suggestions that nitrosothiols function as posttranslational modifications analogous to phosphorylation or acetylation[2]. The bulk of the evidence for protein regulation by S-nitrosylation has relied on in vitro experiments with NO donors, which in some cases also release other reactive oxygen species, or release NO molecules that differ in electronic structure from NO formed by NOS[10]. Additionally, the cytoplasm contains high concentrations of glutathione and metals which can bind NO, making it unclear whether S-nitrosylation can be elicited by endogenously produced NO. Despite these difficulties, Stamler and associates have provided evidence that certain proteins, including the ryanodine receptor[11], caspase-3[12], and albumin[13], possess nitrosothiol moieties in their endogenous state. Unfortunately, the photolytic-chemiluminescence technique employed in these studies[13] was complex precluding widespread application, and it was necessary to purify candidate proteins before assessing their S-nitrosylation state. Thus there is a need in the art for new techniques for measuring this regulatorily important protein modification.

BRIEF SUMMARY OF THE INVENTION

In a first embodiment of the invention a method is provided for assaying nitrosylation of protein substrates. A test sample comprising at least one protein substrate is treated with an alkylthiolating agent to block free thiol groups on the protein substrate. Nitrosothiol bonds on the protein substrate are reduced to form free thiol groups. Alkylthiolating agent is removed from the test sample. Free thiol groups on the protein substrate are reacted with a detectably tagged, activated mixed disulfide, transferring the detectable tag to the protein. The detectable tag on the protein substrate is detected.

In a second embodiment a method for screening for potential drugs useful in modulating protein nitrosylation is provided. A test sample comprising at least one protein substrate is contacted with a test compound. The test sample is treated with an alkylthiolating agent to block free thiol groups on the protein substrate. Nitrosothiol bonds on the protein substrate are reduced to form free thiol groups. Alkylthiolating agent is removed from the test sample. Free thiol groups on the protein substrate are reacted with a detectably tagged, activated mixed disulfide transferring the detectable tag to the protein. The detectable tag on the protein substrate is detected. Amount of detectable tag on the protein substrate is compared to an amount in a control sample similarly treated but not contacted with the test compound. A test compound which increases or decreases the amount of the detectable tag in the test sample relative to the control sample is identified as a modulator of protein nitrosylation.

In another embodiment of the invention a kit for measuring protein nitrosylation is provided. The kit comprises an alkylthiolating reagent and a detectably tagged, activated mixed disulfide reagent. Each reagent is in a separate compartment of the kit.

These and other embodiments of the invention which will be clear to those of skill in the art upon perusing the disclosure, provide the art with convenient methods for determining protein nitrosylation as well as with new physiologically relevant targets for the identification of new drugs involved in apoptosis, neurotoxicity, neurotransmitter release, cellular proliferation, smooth muscle relaxation, and differentiation.

BRIEF DESCRIPTION OF THE DRAWINGS

FIG. 1a, Schematic diagram of the S-nitrosylation assay. A theoretical protein is indicated with cysteines in either the free thiol, disulphide, or nitrosothiol conformation. Following Step 1, free thiols are made unreactive by methylthiolation with MMTS. This modification can be reversed by reduction with 2-mercaptoethanol (2-ME). MMTS is removed in Step 2 by either passing the protein mixture through a spin column or by acetone precipitation. In the final step, nitrosothiols are selectively reduced with ascorbate to reform the thiol, which is then reacted with the thiol-modifying reagent biotin-HPDP, which is drawn schematically. FIG. 1b, GST-H-ras is S-nitrosylated with S-nitroso-acetylpenicillamine (SNAP) in vitro. GST-H-ras was incubated with 1 mM of SNAP or the control compound, N-acetyl-penicillamine (NAP), for one h. The NO donor was removed by passing the protein through a spin column, and the presence of the nitrosothiol bond was confirmed by the presence of an absorption band at ~320 nm. FIG. 1c. GST-H-ras was incubated with vehicle, NAP, or SNAP as in (b) and 100 ng of each protein was subjected the S-nitrosylation assay. After the assay, the samples were resolved by SDS-PAGE and immunoblotted with an anti-biotin antibody. Only S-nitrosylated H-ras was capable of producing a signal in this assay.

FIG. 2a, Brain lysates were incubated with the indicated NO donor, or control compounds, and then subjected to the S-nitrosylation assay. Both classes of NO donor resulted in the S-nitrosylation of an identical subset of proteins. In samples that were not treated with biotin-HPDP, the position of endogenously biotinylated proteins are detectable (arrowheads). FIG. 2b, Identification of S-nitrosylated proteins by mass fingerprinting. Brain lysates were incubated with 40 μM GSNO or GSH, and S-nitrosylated proteins were biotinylated using the S-nitrosylation assay and then purified on streptavidin-agarose followed by 2-ME elution. Individual bands were resolved and purified by SDS-PAGE, trypsinized, and HPLC-purified fragments were used to identify proteins. In some cases, poorly resolved areas revealed multiple proteins.

FIG. 3a, Brain lysates were incubated with 40 μM GSNO or GSH, and S-nitrosylated proteins were biotinylated using the S-nitrosylation assay and then purified on streptavidin-agarose followed by 2-ME elution. 2-ME eluates were blotted with the indicated antibodies. Proteins identified by mass spectrometry were enriched in 2-ME eluates derived from GSNO-treated lysates. FIG. 3b, Control proteins, Rab6 and Rap2, were not detectable in the 2-ME eluates.

FIG. 4a, Brain lysates from nNOS$^{+/+}$ and nNOS$^{-/-}$ mice were subjected to the S-nitrosylation assay, and biotinylated proteins were purified on streptavidin-agarose followed by 2-ME elution. Individual proteins were detected by immunoblotting with the indicated antibodies. The presence of proteins in 2-ME eluates derived from nNOS$^{+/+}$ mice, but not from nNOS$^{-/-}$ mice, indicates a requirement for nNOS in S-nitrosylation. FIG. 4b, Several proteins which are readily S-nitrosylated by NO donors are not detectably S-nitrosylated in either brain lysates from nNOS$^{+/+}$ and nNOS$^{-/-}$ mice.

DETAILED DESCRIPTION OF THE INVENTION

We have developed an assay which can measure nitrosylation of protein substrates in a biological sample. The assay can be performed without purifying individual proteins substrates and without using photolytic-chemiluminescence, greatly simplifying the assay and expanding its applicability to measurement of both in vitro and in vivo nitrosylated proteins.

Figure 1:
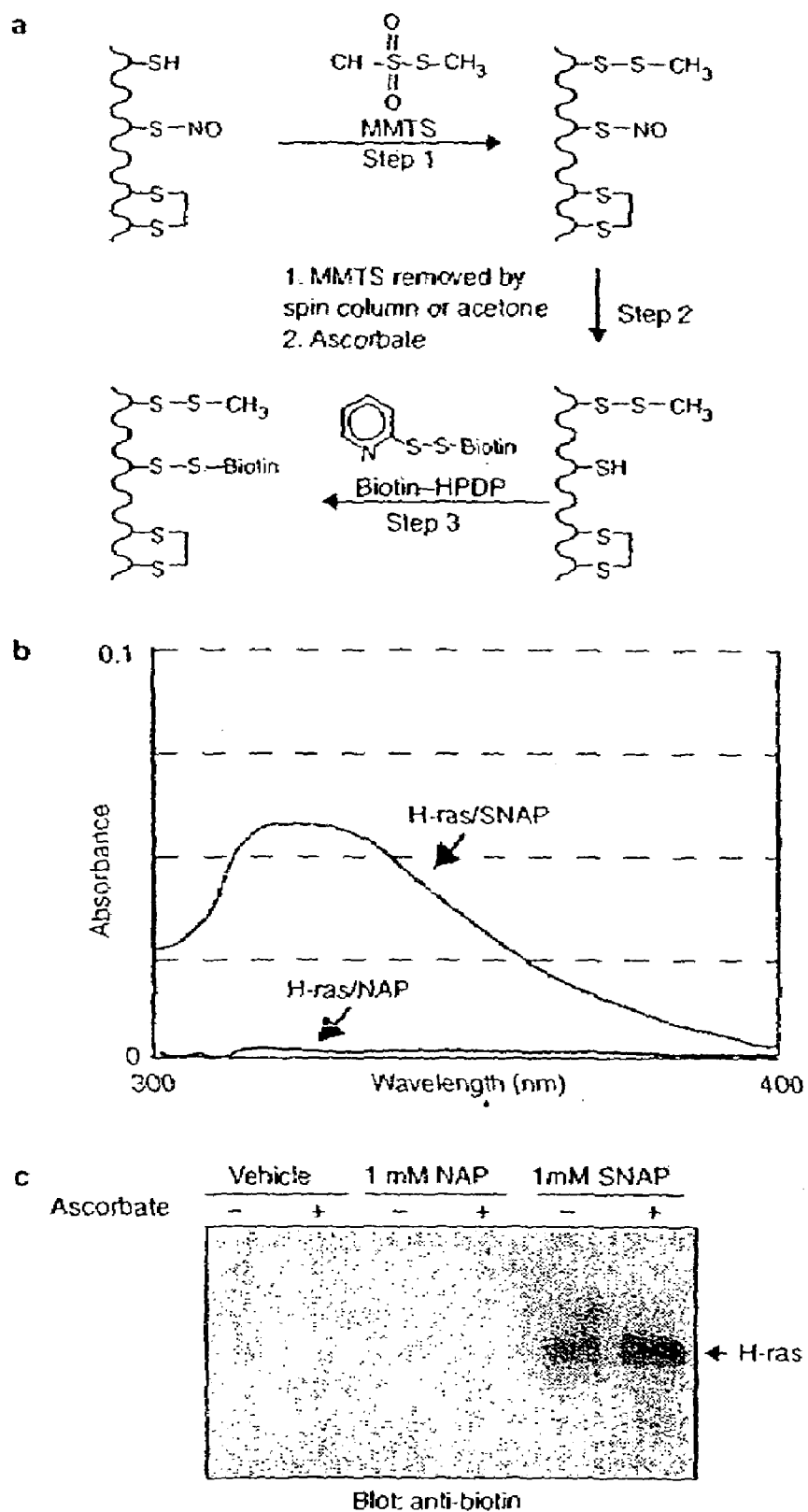
FIG. 1 Detection of S-nitrosylated proteins.

The several step method we have developed to detect S-nitrosylation of proteins employs the conversion of nitrosylated cysteines into detectably tagged cysteines (FIG. 1a). In the first step, free thiols are blocked by incubation with an alkylthiolating agent, such as methyl methanethiosulfonate (MMTS)[14]. Sodium dodecyl sulfate (SDS) can be used to ensure access of alkylthiolating agent to buried cysteines. Under the conditions used, alkylthiolating agent does not react with nitrosothiols or preexisting disulphide bonds[14]. Following the blocking of free thiols, we selectively decompose nitrosothiol bonds with ascorbate, which results in the reduction of nitrosothiols to thiols. The newly formed thiols are then reacted with a detectably tagged, activated mixed disulfide, such as N-[6-(biotinamido) hexyl]-3'-(2'-pyridyldithio)propionamide (biotin-HPDP)[15]. Because alkylthiolating agent can compete with activated mixed disulfide for reacting with thiol groups, it is desirable to remove the alkylthiolating agent completely, for example by a spin column or by acetone precipitation prior to treatment with ascorbate.

Test samples can be lysates of tissues or other crude, purified, or semi-purified biological samples. Preferably the test sample will contain at least one protein which is a substrate for nitrosylation. Preferred samples are those from cells or tissues which express a nitric oxide synthetase, whether neuronal (nNOS), endothelial (eNOS), or inducible (iNOS). Such samples include but are not limited to those made from cells or tissues of brain, blood vessels, and macrophages. Samples may also comprise purified or partially purified proteins including glyceraldehyde-3 phosphate dehydrogenase, creatine kinase, hexokinase-1, glycogen phosphorylase, NR1 and/or NR2 subunits of NMDA glutamate receptor, isoform 2 or 3 of hyperpolarization-activated cation channel (HAC), α1 or α2 subunit of Na+/K+ ATPase, neurofilament H-chain, α or β tubulin, β or γ actin, Retinoblastoma Gene Product (RB), inducible heat shock protein 72, collapsin response mediator protein 1, 2, and/or 4, and calbindin. Other protein substrates which are identified as nitrosylation substrates can also be used.

The assay relies on the detectable tagging of sulfhydryl groups which were formerly nitrosylated. This is accomplished by reducing the nitrosothiol bonds, either spontaneously or catalyzed by ascorbate. The reduced nitrosothiol bonds form free sulfhydryl groups which can be detectably tagged using an activated, mixed disulfide reagent. One such reagent is biotin HPDP, a biotinylated aromatic disulfide reagent. Others as are known in the art can be used. Suitable activating moieties include pyridine, nitropyridine, and nitrobenzoic acid. Suitable tagging moieties include but are not limited to dinitrophenol, biotin, peptide tags, and radiolabels.

In order for the assay to be reliable, the detectable tag moieties must be placed only on formerly nitrosylated thiol groups. To prevent the detectable tag moieties from being placed on free thiol groups present on proteins, such free thiol groups are preferably blocked. One type of blocking agent which can be used is an alkylthiolating agent, such as methyl methanethiosulfonate (MMTS). Such agents may contain any alkyl group and may be derivatized or functionalized. The alkyl group can be straight chain, branched chain, or cyclic. It may contain regions of unsaturation. Other alkylthiolating agents can also be used, as are known in the art. The blocking agent is preferably removed from the test sample prior to the step of the detectable tagging. MMTS, for example, can be removed by acetone precipitation (MMTS remains in the supernatant) or by subjecting the test sample to a spin column.

The detectably tagged protein is detected and or quantified according to any means known in the art. If the detectable tag is biotin, it can be assayed using antibodies specific for biotin or using avidin or streptavidin, its very specific binding partners. Antibodies to other tags such as DNP or peptide tags can also be used. Tagged proteins, for example, can be isolated from affinity or immunoaffinity columns or beads. Particular proteins which are tagged can be identified using antibodies which are specific for those proteins. Any detection means can be utilized, including but not limited to Western blotting. Antibodies can be radiolabeled or fluorescently labeled or enzymatically labeled, as is known in the art.

The assay can be used to screen for potential drugs which are useful in modulating protein nitrosylation. Some proteins are known to be activated and some are known to be inhibited by nitrosylation. The assay can also be used to identify additional proteins which are affected by nitrosylation. Test compounds can be contacted with a biological sample and the effect of the test compounds on the nitrosylation of proteins within the biological sample can be determined. This will typically be done by comparing nitrosylation of proteins within a biological sample to the nitrosylation of proteins within a similar or identical biological sample which has not been treated or contacted with the test compounds. Increases or decreases in the amount of nitrosylation caused by the test sample can be used as an indication of potential usefulness as a drug for modulating protein nitrosylation. Such drugs can be used for modulating such processes as apoptosis, neurotoxicity, neurotransmitter release, cellular proliferation, smooth muscle relaxation, and differentiation.

Kits for assisting those in the art to employ the assay for nitrosylation can comprise a divided container with two or more reagents necessary for the assay in separate compartments. One reagent is an alkylthiolating reagent and another is a detectably tagged, activated, mixed disulfide reagent. Additional reagents can include an antibody specific for biotin, avidin, streptavidin, or for other detectable tags or for proteins substrates. Columns or beads comprising such antibodies, columns or beads comprising avidin, columns or beads comprising streptavidin, spin columns, acetone, polyacrylamide gels, and the like, can optionally be included in the kit. Preferably the alkylthiolating reagent is MMTS and the detectably tagged, activated, mixed disulfide reagent is biotin-HPDP. Instructions for helping users practice the assay method can also be included.

NO has been linked to numerous physiologic and pathologic events not readily explained by the well-established effects of NO on guanylyl cyclase. How might the physiologically S-nitrosylated proteins participate in various NO-mediated events? NO derived from exogenous donors or transfected nNOS inhibits ion flux through the NMDA receptor perhaps via a cysteine in the NR2A subunit that is particularly sensitive to S-nitrosylation[19]. The physiologic S-nitrosylation we observed of the NR2 and NR1 subunits implicates both in mediating the effects of endogenous NO. The cyclic nucleotide-gated HAC channel subfamily is another ion channel which we found to S-nitrosylated by NO donors. Conceivably NO augments its conductance, since the HAC channels resemble the olfactory cyclic nucleotide-gated channel[20] which is activated by NO[6].

Studies using nNOS[-/-] mice and nNOS inhibitors indicated a physiologic role for NO in cell growth and differentiation[21,22] but molecular targets mediating such events have not been established. Physiologic S-nitrosylation of the CRMP proteins, which might influence process formation in neurons, might explain the impaired dendrite outgrowth of nNOS[-/-] mice[23]. The organomegaly of NOS deficient *Drosophila* appears to be due to NO-mediated activation of the cell-cycle arrest activity of Rb[24]. The observation that Rb is S-nitrosylated suggests a direct regulation of Rb by NOS in this system. In mammals, Rb S-nitrosylation might participate in the cytostatic influence of NO on vascular smooth muscle that may prevent intimal hyperplasia and subsequent atheroma formation[21]. Effects of S-nitrosylation on HSP72 are not known.

Excess release of NO leads to metabolic compromise and cell death, especially in the nervous system[25]. The S-nitrosylated targets we have identified might mediate such effects. For instance S-nitrosylation of creatine kinase and GAPDH inhibits their activity[7,26]. By contrast, glycogen phosphorylase activity is augmented by NO[27] which would increase glucose-1-phosphate levels and deplete intracellular stores of glycogen. The membrane depolarization associated with NO-mediated cell death might reflect decreased sodium pump activity as S-nitrosylation of the sodium pump inhibits its activity[28].

NO has been linked to cytoskeletal alterations driving neuronal remodeling and apoptosis, as NO donors elicit "cytoskeletal breakdown" in cerebellar granule cells with actin filament dissolution and microtubule destabilization[29]. In skeletal muscle, NO impairs calcium-dependent activation of actin filaments[30]. The physiologic S-nitrosylation of structural proteins such as NF—H, tubulin, and actin might mediate these effects.

Why are some proteins more readily S-nitrosylated than others? Conceivably, proteins with disproportionately high numbers of cysteines would be more susceptible to S-nitrosylation, but none of the proteins we have detected are notably rich in cysteine, and cysteine-rich proteins were not detected. The differential reactivity of various cysteines towards NO may reflect their variable access to NO as well as their nucleophilicty, which is determined by hydrogen bonding interactions with the thiol. Stamler, Lipton, and associates[2] recently proposed that residues adjacent to cysteines in proteins increase the nucleophilic properties of cysteine with putative consensus sequences adjacent to the cysteine providing enhanced susceptibility to S-nitrosylation[2].

Adapter proteins may provide access of NOS to S-nitrosylation targets. Analogously, A-kinase anchoring proteins (AKAPs) bind to both kinases and their substrates facilitating specificity in the kinase reactions[31]. Our finding that NR2A is endogenously S-nitrosylated is notable as this subunit is coupled to nNOS by PSD95[32]. Conceivably, proximity of the S-nitrosylation target to nNOS, mediated by adapters such as PSD95 or CAPON[33], may also determine physiologic S-nitrosylation.

Our findings indicate that S-nitrosylation is a posttranslational modification which occurs on proteins that mediate several important physiologic processes. The sensitivity, specificity, and simplicity of the S-nitrosylation assay may facilitate elucidation of regulatory mechanisms for S-nitrosylation signaling, including signals that physiologically stimulate S-nitrosylation as well as those that lead to denitrosylation.

EXAMPLES

Example 1

Methods

Preparation of S-Nitroso-H-ras

GST-H-Ras was prepared in *E. coli*, bound to glutathione agarose, and eluted with 10 mM glutathione as described[33]. Glutathione was removed by passing the material through a MicroBioSpin-6 column (Biorad) equilibrated in HEN buffer (250 mM Hepes, pH 7.7, 1 mM EDTA, 0.1 mM neocuproine). GST-H-ras was incubated with 100 $\mu$M SNAP, 100 $\mu$M NAP, or the DMSO vehicle for 1 h at room temperature in the dark. The SNAP or NAP was removed by passing the material through a spin column as above three times.

S-Nitrosylation Assay

Freshly isolated rat cerebella was homogenized in 50 volumes HEN buffer and then centrifuged at 800 g for 10 min at 4° C. The supernatant typically contained 0.8 $\mu$g protein per $\mu$l based on the BCA protein assay and was adjusted to 0.4% CHAPS. To 100 $\mu$l of the supernatant was added the appropriate concentration of the NO donor or control compound in a volume of 5 $\mu$l, and the mixture was incubated for one h at 25° C. Following this step, the NO donor was removed by centrifuging the suspension through a MicroBioSpin6 column preequilibrated in HEN buffer. To the eluate was added four volumes of blocking buffer (9 volumes of HEN buffer plus 1 volume 25% SDS, adjusted to 20 mM MMTS with a 2 M stock prepared in dimethylformamide (DMF)) at 50° C. for 20 min with frequent vortexing. The MMTS was then removed by desalting three times with the MicroBioSpin6 column preequilibrated in HEN buffer. To the eluate was added biotin-HPDP prepared fresh as a 4 mM stock in dimethylsulfoxide from a 50 mM stock suspension in DMF. Sodium ascorbate was added in a final volume of 1 µl to a final concentration of 1 mM. Ascorbate incubated with 1 mM oxidized glutathione in HEN buffer for one h failed to reduce 5,5'-dithio-bis(2-nitrobenzoic acid) (DTNB), a calorimetric thiol probe, indicating that under the conditions used, ascorbate does not reduce disulphides (S.R.J. and S.H.S., data not shown). After incubation for one h at 25° C., SDS-PAGE sample buffer was added and the samples were resolved by SDS-PAGE and transferred for immunoblotting. Because the cysteine biotinylation in this assay is reversible, SDS-PAGE sample buffer was prepared without reducing agents. Additionally, to prevent nonspecific reactions of biotin-HPDP, samples were not boiled prior to electrophoresis. All steps preceding SDS-PAGE were performed in the dark. To determine the stability of nitrosothiols during the blocking step, we prepared blocking reactions comprising 0.8 ml blocking buffer and either 0.2 ml HEN buffer or 0.2 ml GSNO solution (20 mM GSNO in HEN buffer). Following the blocking step, nitrosothiol content was reduced ~25% as determined by the reduction in absorbance at 300 nM of heated samples compared to unheated samples.

Because H-ras contains only the common 20 amino acids, we wanted to examine the possibility that noncanonical amino acids produce nonspecific signals in our assay. We tested the ability of selenocysteine, prepared by reduction of selenocystine, to be blocked by MMTS. We detected modification of selenocysteine by MMTS by thin-layer chromatography (TLC) consistent with the idea that selenocysteine is similar in chemical reactivity to cysteine[34] and that selenocysteine would be blocked in Step 1 in a manner identical to cysteine residues. Mixed pyridyl disulphides, such as that found in biotin-HPDP, have been reported to react selectively with thiols[15]. To confirm that cysteine sulfate, cysteine sulfinic acid or selenomethionine do not react with biotin-HPDP, we incubated these compounds at 1 mM with an identical amount of biotin-HPDP in HEN buffer and reaction of the compounds with biotin-HPDP was determined by spectrophotometric detection of the released 2-thiopyridone[15]. Cysteine sulfate and selenomethionine at 1 mM failed to react with biotin-HPDP. Cysteine sulfinic acid reacted weakly, but was found to react with MMTS by TLC, indicating that these residues would be blocked in Step 1.

Purification of S-Nitrosylated Proteins

Approximately 10 g of brain tissue were S-nitrosylated and biotinylated as above except that no CHAPS was used, and MMTS was removed by a single acetone precipitation step comprising 2 vol of –20° C. acetone for 30 minutes at –20° C., followed by centrifugation at least 1,500 g. Pellets were resuspended in 4 ml HENS buffer (25 mM Hepes, pH 7.7, 0.1 mM EDTA, 10 µM neocuproine, 1% SDS) per g of tissue prior to biotinylation with biotin-HPDP. Following biotinylation to label S-nitrosylated proteins, biotin-HPDP was removed by acetone precipitation followed by centrifugation, and the pellet was resuspended in HENS buffer as above. Two volumes of neutralization buffer (20 mM Hepes, pH 7.7, 100 mM NaCl, 1 mM EDTA, 0.5% Triton X-100) was added and streptavidin-agarose (Sigma) was added to purify biotinylated proteins. In some experiments, neutravidin-agarose (Pierce) was used with identical results. Biotinylated proteins were incubated with the resin for one h at room temperature, washed 5 times with neutralization buffer adjusted to 600 mM NaCl, and then incubated with elution buffer (20 mM Hepes, pH 7.7, 100 mM NaCl, 1 mM EDTA, 100 mM 2-mercaptoethanol) to recover the bound protein.

In experiments to detect endogenously S-nitrosylated proteins, lysates were prepared as above from a minimum of 750 mg of tissue derived from nNOS$^{-/-}$ or nNOS$^{+/+}$ wild-type mice, without addition of NO donors. nNOS$^{-/-}$ mice[18] were backcrossed a minimum of seven times against the C57/BL6 strain, which was the strain used for wild-type controls. Proteins were typically eluted with 100 mM 2-ME in a volume of 100 µl and roughly one third was loaded on gels for immunoblotting. The starting material on these gels comprised 1/500 of the material applied to the streptavidin agarose. In some experiments, 1 mM MMTS was included in the lysis buffer to reduce denitrosylation during homogenization and to reduce post-homogenization S-nitrosylation from tissue-derived nitrite, but was not found to effect the yield of S-nitrosylated proteins (S.R.J. and S.H.S., unpublished data).

Of the 15 proteins identified as sensitive to S-nitrosylation, 13 were chosen for further in vitro S-nitrosylation and endogenous S-nitrosylation studies based on whether antibodies were commercially available. In cases where more than one isoform of a protein was identified, one isoform was selected for study. Antibodies for hexokinase 1, NR1, NR2A; glycogen phosphorylase; HSP70, NF—H; Rb; actin, β-tubulin, calbindin; Na$^+$/K$^+$ ATPase α2 subunit; creatine kinase; were from Chemicon (Temecula, Calif.), Advanced ImmunoChemical Inc. (Long Beach, Calif.), NeoMarkers (Union City, Calif.), Pharmingen (San Diego, Calif.), Sigma (St. Louis, Mo.), Upstate Biotechnology (Lake Placid, N.Y.), Fitzgerald Industries (Concord, Mass.), respectively.

Mass Spectrometry

Top 'major' experimental masses (m/z) combined from MALDI-ReTOF MS experiments were used to search a non-redundant protein database using the Peptide Search Algorithm[35]. Rat brain Na$^+$/K$^+$ ATPase α2 subunit was identified (NCBI ID# 6978545) with 20 discrete peptides. The α1 subunit (NCBI ID# 6978543) was identified with a partial overlap with α1 and also 15 additional peptides. The mouse hyperpolarization-activated cation channel was identified with 8 peptides which aligned to HAC2. Four additional peptides, along with peptides which overlap those found with HAC2, aligned to HAC3 (NCBI ID# 3242242). Rat brain hexokinase1 (NCBI ID# 6981022) was identified with seven peptides. NR1 (NCBI ID# 228224) was identified with six peptides. Rat brain NF—H(NCBI ID# 112044) was identified with 25 peptides. Rat NR2 was identified with seven peptides, but did not specifically identify a distinct isoform. Rat Rb (NCBI ID# 6686304) was identified with 12 peptides. Rat brain calbindin (NCBI ID# 115396) was identified with 15 peptides. Rat GAPDH (NCBI ID# 4176768) was identified with six peptides. β-actin (NCBI ID# 49868) was identified with eight peptides, and eight, including one distinct peptide, identified γ-actin (NCBI ID# 809561). Rat creatine kinase (NCBI ID# 6978659) was identified with nine peptides. β-tubulin (NCBI ID# 5174735) was identified with 12 peptides, and ten identified α-tubulin (NCBI ID# 223556). In bands that identified CRMP (also referred to as dihydropyrimidinase-related protein, and TOAD-64), CRMP-2 (SwissProt P47942) was identified with 25 peptides, CRMP-1 (NCBI ID# 3122017) with nine; CRMP-4 (NCBI ID# 3122044) with six. Rat HSP72 (NCBI ID# 347019) was identified with 12 peptides. Rat brain glycogen phosphorylase (NCBI ID# 6686304) was identified with 12 peptides. In several preparations for high molecular weight proteins, some peptides were purified that did not match known proteins in that rodent database indicating that additional S-nitrosylated proteins were detected by our assay.

Detailed Protocol

Materials

In Vitro S-Nitrosylation
  N-[6-(biotinamido)hexyl]-3'-(2'-pyridyldithio)propionamide (biotin-HPDP)
  CHAPS
  Dimethylformamide
  Dimethylsulfoxide (DMSO)
  Methyl methanethiosulfonate (MMTS)
  MicroBioSpin6 columns (Biorad)
  Neocuproine (Sigma)
  NO donor GSNO (Sigma)
  Glutathione (GSH) (Sigma)
  Sodium ascorbate Detection of S-Nitrosylated Proteins
  Anti-biotin mouse monoclonal antibody (Sigma)

Purification of S-Nitrosylated Proteins
  Streptavidin agarose (Sigma) or Neutravidin (Pierce)

Recipes

Recipe 1: HEN Buffer

| Hepes-NaOH pH 7.7 | 250 mM |
|---|---|
| EDTA | 1 mM |
| Neocuproine (Sigma) | 0.1 mM |

Recipe 2: CHAPS Stock
  Prepare a 10% solution in $dH_2O$.

Recipe 3: MMTS Stock
  Prepare a 2-M solution in dimethylformamide.

Recipe 4: Blocking Buffer

| HEN buffer | 9 volumes |
|---|---|
| SDS (25% w/v in $H_2O$) | 1 volume |

Adjust to 20 mM MMTS with MMTS Stock (Recipe 2).

Recipe 5: HENS Buffer
  Adjust HEN buffer to 1% SDS by addition of 1/25 volume of a 25% (w/v) SDS solution.

Recipe 6: Ascorbate Solution
  Prepare a 50-mM solution of sodium ascorbate in deionized water.

Recipe 7: Biotin-HPDP Stock
  Prepare N-[6-(biotinamido)hexyl]-3'-(2'-pyridyldithio)propionamide (biotin-HPDP) (Pierce) as a 50 mM suspension in DMF. Freeze at −20° C. until needed.

Recipe 8: Labeling Solution

Just before use thaw the stock suspension of biotin-HPDP and vortex to resuspend the biotin-HPDP. Dilute with DMSO to a final concentration of 4 mM. Vortex to ensure that the biotin-HPDP is in solution.

Recipe 9: SDS-PAGE Sample Buffer-Without Reducing Agents

| 50 mM Tris-HCl, pH 6.8 | 7 ml |
|---|---|
| Glycerol | 3 ml |
| SDS | 1.028 g |
| Bromophenol blue | 1.2 mg |

Other sample buffers may be appropriate depending on the type of gel system used, however, the sample buffer must be made without 2-ME or DTT.

Recipe 10: Neutralization Buffer

| Hepes-NaOH, pH 7.7 | 20 mM |
|---|---|
| NaCl | 100 mM |
| EDTA | 1 mM |
| Triton X-100 | 0.5% |

Recipe 11: Neutralization Buffer+NaCl
  Prepare Neutralization Buffer (Recipe 11) with 600 mM NaCl.

Recipe 12: Elution Buffer

| Hepes-NaOH, pH 7.7 | 20 mM |
|---|---|
| NaCl | 100 mM |
| EDTA | 1 mM |
| 2-ME | 100 mM |

Instructions

Preparation of Protein Samples
  The following steps are performed at 4° C. Protein samples can be obtained from homogenized tissue and can include or exclude the membrane fragments. Alternatively, purified proteins may be used providing any low molecular thiol contaminants have been removed.

Preparation of Cytosolic Proteins
  1. Homogenize the tissue in approximately 20 volumes of HEN buffer (Recipe 1).
  2. Centrifuge at 100,000 g for 1 h at 4° C.
  3. Recover the supernatant.
  4. Assay for protein concentration using the Biuret or other method.
  Note: Protein concentration must not exceed 0.8 µg per µl. Add HEN Buffer (Recipe 1) to adjust concentration as needed.

Preparation of Membrane Fragments and Cytosolic Proteins
  1. Homogenize the tissue in approximately 20 volumes of HEN buffer (Recipe 1).
  2. Centrifuge at 2,000 g for 10 min. at 4° C.
  3. Recover the supernatant.
  4. Assay for protein concentration using the Biuret or other method.

Note: Protein concentration must not exceed 0.8 µg per µl. Add HEN Buffer (Recipe 1) to adjust the concentration as needed.

5. Adjust the sample to 0.4% CHAPS with a 10% stock (Recipe 2). Vortex the sample to dissolve any membrane constituents. Avoid introducing bubbles while vortexing.

Note: This ensures that the gel filtration columns used for removing NO donors will work properly.

Preparation of Purified Proteins

To use a purified protein, ensure that low molecular weight thiols, such as 2-ME, dithiothreitol, or glutathione have been removed.

1. Dialyze the protein against HEN Buffer (Recipe I) or exchange the protein solution with a HEN Buffer-equilibrated MicroBioSpin 6 column following the instructions of the manufacturer.
2. Recover the sample.
3. Assay for protein concentration using the Biuret or other method.

Note: Protein concentration must not exceed 0.8 µg per µl. Add HEN Buffer (Recipe 1) to adjust the concentration as needed.

In Vitro S-Nitrosylation

1. Add NO donor (GSNO) or inactive donor control (GSH) to 100 µl protein sample to achieve a range of final concentrations from 0.1 µM to 100 µM. At this point, all samples should be protected from light by covering tubes and containers in foil, or by doing the experiments in a dark room.

Note: S-nitrosylation signals obtained with 1 µM or less of NO donor are more likely to represent physiologic targets. NAP is included as a negative control.

Note: The NO donor should be protected from light and frozen at −80° C. when not in use.

Note: Other NO donors are acceptable, such as S-nitroso-N-acetylpenicillamine (Sigma) or 1-[2-(2-aminoethyl)-N-(2-ammonioethyl)amino]diazen-1-ium-1,2-diolate (DETA NONOate) (Alexis Chemicals), and are used at similar concentrations as GSNO.

2. Incubate in the dark to prevent light-induced degradation of the NO donors or protein nitrosothiols for 20 min at room temperature.

Biotinylation of S-Nitrosylated Proteins

Removal of the NO Donor

It is advisable to remove the NO donor at this time because the donor may nitrosylate cysteines that are physiologically inaccessible after the proteins are denatured in the next step. To remove the NO donor, acetone precipitation can be used, followed by resuspension of the pellet in the starting volume of HENS buffer (Recipe 5), but for samples of less than 100 µl, we use spin columns, such as the MicroBioSpin 6 column. One column is prepared for every condition used above. The column preparation and use is performed as recommended by the manufacturer.

1. Mix the resin to form a suspension.
2. Allow the resin to settle, remove the supernatant, and resuspend in 500 µl of HEN Buffer (Recipe 1).
3. Allow the resin to settle, remove the supernatant, and resuspend in another 500 µl of HEN Buffer (Recipe I).
4. Apply the sample (in a volume of 75 µl) to the center of the resin.
5. Centrifuge the column at 1,000 g for 4 min.
6. Recover the sample.

Blocking of Protein Samples

1. Add four volumes of Blocking Buffer (Recipe 4).
2. Incubate at 50° C. for 20 min vortexing frequently.
3. Remove the MMTS by acetone precipitation. To the sample, add 10 volumes of acetone, prechilled to −20° C. Incubate for 20 min at −20° C., followed by centrifugtion at at least 2,000 g for 10 min at 4° C. Resuspend the pellet in 0.1 ml HENS buffer per mg of protein in the starting sample.
4. Alternatively, for samples in a volume less than 100ll, remove MMTS by exchanging the blocking solution with HEN Buffer (Recipe 1) three times with three MicroBio-Spin6 columns preequilibrated in HEN buffer. Final volume of the third eluate should be approximately 50–70 µl.

Biotinylation of Nitrosothiols

1. Prepare Labeling Solution (Recipe 8) just before use. Vortex before use to ensure even suspension of the Biotin-HPDP.
2. To the blocked protein sample, add one third volume Labeling Solution (Recipe 8) and one-fiftieth volume Ascorbate Solution (Recipe 6) and incubate for 1 h at 25° C. At this point, samples do not need to be protected from light.
3. As a control treat some samples with DMF vehicle solution.

Detection of Biotinylated Proteins by Immunoblotting

1. Add SDS-PAGE sample buffer (Recipe 9) without reducing agents.

Note: Do not boil samples or use reducing agents in the SDS-PAGE sample buffer. We recommend that sample buffer is added directly to samples and they are immediately loaded onto the gel.

2. Perform SDS-PAGE.
3. Transfer the electrophoresed samples to nitrocellulose for immunoblotting.
4. Detect the biotinylated proteins with anti-biotin mouse monoclonal antibody.

All steps preceding SDS-PAGE were performed in the dark.

Purification of Biotinylated Proteins

1. Remove biotin-HPDP by adding two volumes of acetone for twenty minutes at −20° C. Centriffuge the sample at at least 2,000 g for 10 minutes at 4° C. Discard the supernatant, which contains the biotin-HPDP, and gently rinse the walls of the tube, as well as the surface of the pellet with −20° C. acetone to remove traces of Biotin-HPDP.
2. Resuspend the pellet in 0.1 ml of HENS Buffer (Recipe 5) per mg of protein in the initial protein sample.
3. Add two volumes of Neutralization Buffer (Recipe 10).
4. Add 15 µl of packed streptavidin-agarose per mg of protein used in the initial protein sample to purify biotinylated proteins.

Note: Neutravidin-agarose (Pierce) has been used with identical results.

5. Incubate the biotinylated proteins with the resin for 1 h at room temperature.
6. Wash the beads 5 times with 10 vol of Neutralization Buffer+NaCl (Recipe 11). Centrifuge at 200 g for 5 sec at room temperature between each wash.
7. Incubate the beads with Elution Buffer (Recipe 12) to recover the bound proteins.
8. Add SDS-PAGE sample buffer with reducing agent.
9. Perform SDS-PAGE.
10. Transfer the electrophoresed samples to nitrocellulose for immunoblotting.
11. Stain the nitrocellulose with Ponceau S and excise the proteins or test for the protein of interest with specific antibodies.

Related Techniques

Detection of Endogenous S-Nitrosothiols

To detect endogenously S-nitrosylated proteins, protein samples can be prepared as described above from a minimum of 750 mg of tissue derived from nNOS[-/-] or nNOS[+/+] wild-type mice, without the addition of NO donors. Because no NO donor is added, following the preparation of the protein sample, the procedure begins with the blocking step ("Blocking of protein samples") and then biotinylation ("Biotinylation of nitrosothiols"). The biotinylated proteins are purified following the steps outlined in the "Purification of biotinylated proteins", and can be immunoblotted with antibodies against candidate proteins whose nitrosylation status is being queried. Additionally, samples are protected from light immediately following homogenization, up until the biotin-HPDP Labeling Solution is added.

Troubleshooting

False Positive Signals

This S-nitrosylation assay is based on the assumption that only an S-nitrosylated cysteine residue will become biotinylated following the various treatments described above. However, if all cysteines have not been successfully blocked with the methylthiolating reagent, MMTS, then non-nitrosylated cysteines may produce a signal in this assay. SDS is included to promote denaturation, which should ensure accessibility of MMTS to each thiol. A cysteine that is inaccessible to MMTS may become accessible to biotin-HPDP during the labeling step if time-dependent or DMSO-dependent denaturation occurs and results in the unhindered exposure of a thiol. To ensure the maximal accessibility of cysteines to MMTS, a minimum ratio of SDS to protein is essential to ensure maximal protein denaturation. Thus, protein samples that exceed 0.8 $\mu g/\mu l$ are more prone to be incompletely blocked by MMTS.

Negative Controls for In Vitro Nitrosylation

The best way to ensure that a signal is due to S-nitrosylation is to include an inactive NO-donor control. Thus, in experiments designed to detect proteins susceptible to S-nitrosylation in brain extracts (FIG. 1B), the NO donor was GSNO and the inactive compound was the corresponding denitrosylated molecule NAP. A vehicle control is also useful, because the inactive control compound (GSH) is a thiol-containing molecule, which may have effects on cellular thiols and nitrosothiols. Bands that are present in the NO donor lane, but not in lanes in which control compounds were used, represent proteins that are S-nitrosylated.

Negative Controls for Detection of In Vivo Nitrosylation

Because the nitrosylation assay includes biotin immunoblotting, proteins that are endogenously biotinylated, can be a source of significant background. These enzymes, which perform carboxytransferase reactions, are found at different levels in different animals. For example, the brains of C57/BL6 mice contain these endogenously-biotinylated proteins at levels 20 times higher than that found in Norweigen white rats. The presence of endogenously-biotinylated proteins can actually be beneficial, because they can serve as loading controls. That is, their uniform intensity in different lanes can ensure that equivalent amounts of protein were utilized in different experiments. A key control in the identification of these proteins is the use of a DMF vehicle control, instead of biotin-HPDP, in the biotinylation labeling reaction. A blocked sample that has been subjected to DMF treatment, rather than biotin-HPDP treatment shows two bands, which represent endogenously biotinylated proteins (FIG. 1B).

This protocol outlines the methods for the detection of both in vitro S-nitrosylated proteins, by biotin immunoblotting, and endogenously biotinylated proteins, by purification of S-nitrosylated proteins by streptavidin-affinity chromatography followed by candidate-specific immunoblotting. In this latter method, some of the same troubleshooting issues arise, but the required controls are different. To ensure that a signal is due to NOS activity and not due to incomplete blocking, tissue samples that are devoid of NOS are ideal. Thus, protein samples prepared from NOS[-/-] mice, provide ideal controls. Alternatively, if NOS-transfected tissue culture cells are used, mock transfected cells would be useful. If these types of controls are unavailable, then samples prepared with NOS inhibitors, such as nitroarginine, can also be used as negative controls.

Example 2

Assay Validation

As an initial test of the system, we prepared S-nitroso-H-ras by incubation with NO donors. H-ras treated with S-nitrosoacetylpenicillamine (SNAP) is readily S-nitrosylated on a single cysteine[5] which is detected spectrophotometrically by the characteristic absorbance of its nitrosothiol moiety (FIG. 1b). Reduced H-ras is prepared by incubating H-ras with the control compound N-acetylpenicillamine (NAP). In the S-nitrosylation assay, S-nitroso-H-ras is biotinylated (FIG. 1c), while H-ras, which lacks the nitrosothiol moiety, is unreactive. Ascorbate enhances the reactivity of S-nitroso-H-ras in the assay consistent with the idea that ascorbate accelerates the rate of nitrosothiol decomposition. Ascorbate does not appear to be essential for biotinylation in this assay, presumably because of spontaneous nitrosothiol decomposition. The specific biotinylation of the S-nitrosylated protein indicates that only S-nitrosylated proteins are capable of producing a signal in this assay.

Example 3

Identification of Proteins Sensitive to Exogenous Nitrosylation

Figure 2:
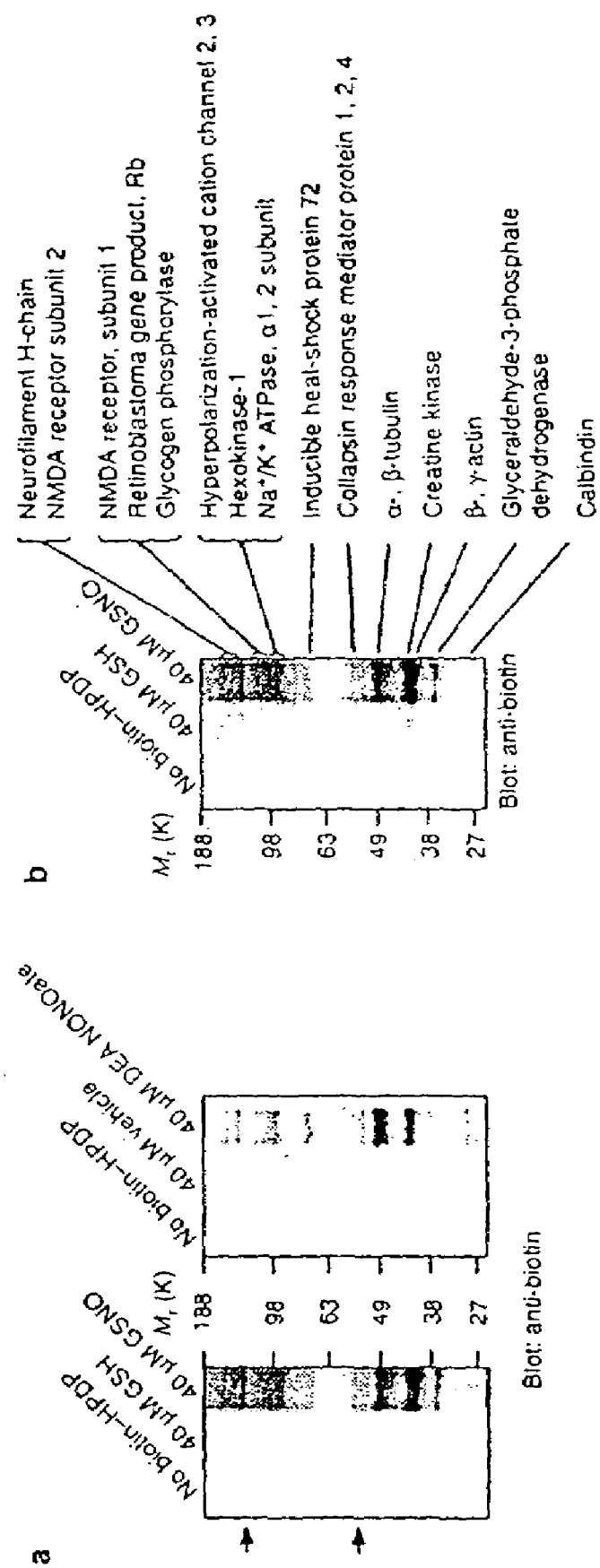
FIG. 2 S-nitrosylation of proteins in a brain lysate with GSNO and DEA-NONOate and their identification by mass fingerprinting.

To identify tissue proteins that are uniquely sensitive to S-nitrosylation, we reacted brain lysates with NO donors of two different classes, 2-(N,N-diethylamino)-diazenolate-2-oxide (DEA-NONOate) and S-nitroso-glutathione (GSNO). GSNO is present in the brain at micromolar concentrations and might serve as an endogenous reservoir of NO groups[16] and S-nitrosylate proteins by direct transnitrosation of thiols[17]. Following incubation with the NO donors, the tissue was passed through a spin column to remove the NO donors and then subjected to the S-nitrosylation assay. Biotinylated proteins were detected by immunoblotting with a biotin-specific antibody (FIG. 2a). A group of ~15 protein bands are S-nitrosylated following treatment with either class of NO donor. In tissue preps subjected to the S-nitrosylation assay but in which the biotin-HPDP was omitted, faint reactivity of certain bands are visible, representing endogenously biotinylated proteins. With the limited exposure time used, no biotinylated proteins are detected in samples treated with control compounds or solvent vehicles. The absence of biotinylated proteins in these control samples indicate that the vast majority of thiols are blocked by MMTS and thus unable to produce a signal with biotin-HPDP.

To identify the S-nitrosylated proteins, we treated brain preparations with GSNO and subjected the tissue to the S-nitrosylation assay. Biotinylated proteins were purified on streptavidin-agarose and then selectively eluted with 2-mercaptoethanol (2-ME), which cleaves the disulphide linkage formed by biotin-HPDP. Endogenous disulphides and cysteines modified by MMTS are also reduced to cysteine during the 2-ME elution step. Following SDS-PAGE, the predominant bands were trypsinized, and the peptides were subjected to matrix-assisted laser desorption/ionization reflectron time-of-flight mass spectrometry (MALDI-Re-TOF MS) for mass fingerprinting.

The S-nitrosylated proteins comprise both cytosolic and membrane-associated proteins (FIG. 2b). They include metabolic enzymes such as GAPDH, creatine kinase, hexokinase1, and glycogen phosphorylase; ion channels such as the NR1 and NR2 subunits of the N-methyl-D-aspartate (NMDA) glutamate receptor, the hyperpolarization-activated cation channel (HAC) isoforms 2 and 3, and the sodium pumping enzyme $Na^+/K^+$ ATPase $\alpha$1 and $\alpha$2 subunits; and structural proteins such as neurofilament heavy chain (NF—H), $\alpha$-, and $\beta$-tubulin and $\beta$-, and $\gamma$-actin. We also detect signaling proteins such as the retinoblastoma gene product (Rb), heat shock protein-72 (HSP72), the collapsin response mediator protein (CRMP), isoforms 1,2, and 4, and calbindin. Some proteins which have previously been shown to be susceptible to in vitro S-nitrosylation, such as H-ras[5] and caspase-3[12], were not detected in our assay. This may due to poor S-nitrosylation of these proteins at the low concentrations of GSNO used in our experiments, or a low abundance of these proteins in the brain homogenates that were subjected to in vitro S-nitrosylation.

Example 4

Confirmation of Protein Identification

Figure 3:
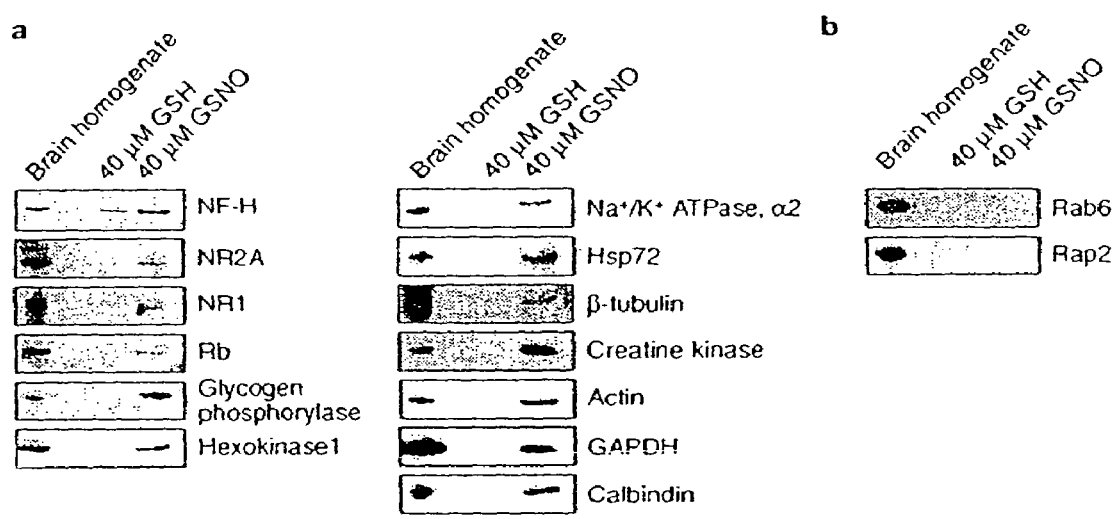
FIG. 3 In vitro S-nitrosylation assays identify proteins susceptible to S-nitrosylation.

As additional evidence that the proteins identified by mass fingerprinting are S-nitrosylated, we performed the S-nitrosylation assay on brain lysates treated with GSH or GSNO, purified labeled protein on streptavidin-agarose, and blotted the 2-ME eluates for selected proteins identified in by mass fingerprinting. Proteins identified by mass fingerprinting are detected in the GSNO-treatment-derived 2-ME eluates but not in the GSH-derived eluates (FIG. 3a). The G proteins Rap2 and Rab6 contain cysteines but are not S-nitrosylated under our experimental conditions (FIG. 3b), establishing the specificity of the assay.

Example 5

Endogenous Nitrosylation of Proteins Detected

In initial experiments utilizing NO donors, we did not detect S-nitrosylated bands in the absence of donors, presumably because endogenous nitrosothiols are present at substantially lower levels than the nitrosothiols that form following in vitro treatment with NO donors. Moreover, the robust S-nitrosylation obtained with NO donors leads to detection of nitrosothiols with a very short autoradiographic exposure, which is not lengthy enough to detect endogenous S-nitrosylation.

To determine if the proteins that we identified as susceptible to S-nitrosylation by NO donors are S-nitrosylated by endogenously-generated NO, we prepared brain extracts from $nNOS^{+/+}$ mice and mice with targeted deletion of neuronal NOS ($nNOS^{-/-}$)[18]. Lysates were subjected to the S-nitrosylation assay procedure and the biotinylated proteins were purified on streptavidin-agarose, eluted with 2-ME, and immunoblotted with antibodies to the putative S-nitrosylated proteins (FIG. 4a).

Figure 4:
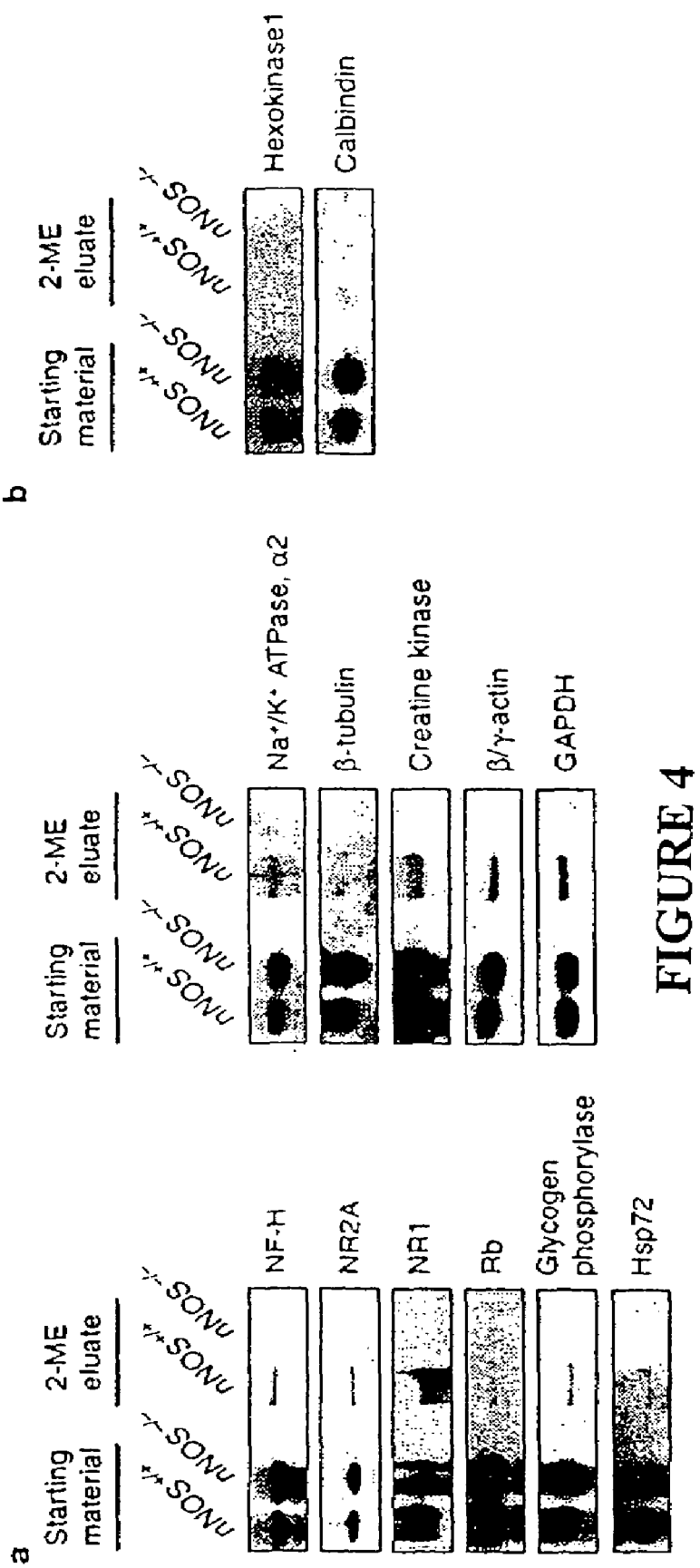
FIG. 4 Endogenous S-nitrosylation is mediated by nNOS.

In 2-ME eluates derived from $nNOS^{+/+}$ mice we detect GAPDH, glycogen phosphorylase, creatine kinase, Rb, HSP72, $Na^+/K^+$ ATPase $\alpha$2 subunit, NR2A, NR1, $\beta$-tubulin, actin, and NF—H (FIG. 4). These proteins are absent in the 2-ME eluates prepared from $nNOS^{-/-}$ mice. Thus, some of the proteins which are S-nitrosylated by NO donors are also S-nitrosylated by endogenously generated NO. Interestingly, while hexokinase1 and calbindin are robustly S-nitrosylated by NO donors, we do not find that they are endogenously S-nitrosylated (FIG. 4b). Conceivably they are endogenously S-nitrosylated but the nitrosothiol modification is especially labile. Alternatively, these proteins might reside in cellular compartments that are not exposed to sufficiently high concentrations of endogenous NO to be effectively S-nitrosylated.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

REFERENCES

1. Denninger, J. W. & Marletta, M. A. *Biochim. Biophys. Acta* 1411, 334–350 (1999).
2. Stamler, J. S., Toone, E. J., Lipton, S. A. & Sucher, N. J. *Neuron* 18, 691–696 (1997).
3. Stamler, J. S. et al. *Proc. Natl. Acad. Sci. U.S.A.* 89, 444–448 (1992).
4. Mayer, B. et al. *J. Biol. Chem.* 273, 3264–3270 (1998).
5. Lander, H. M. et al. *J. Biol. Chem.* 272, 4323–4326 (1997).
6. Broillet, M. C. & Firestein, S. *Neuron* 16, 377–385 (1996).
7. Molina y Vedia, L. et al. *J. Biol. Chem.* 267, 24929–24932 (1992).
8. Kashiba-Iwatsuki, M. et al. *J. Biochem.* (*Tokyo*) 122, 1208–1214 (1997).
9. Dicks, A. P. & Williams, D. L. *Chem. Biol.* 3, 655–659 (1996).
10. Feelisch, M. *Naunyn Schmiedebergs Arch. Pharmacol.* 358, 113–122 (1998).
11. Xu, L., Eu, J. P., Meissner, G. & Stamler, J. S. *Science* 279, 234–237 (1998).
12. Mannick, J. B. et al. *Science* 284, 651–654 (1999).
13. Stamler, J. S. et al. *Proc. Natl. Acad. Sci. U.S.A.* 89, 7674–7677 (1992).
14. Kenyon, G. L. & Bruice, T. W. *Methods Enzymol.* 47, 407–430 (1977).
15. Stuchbury, T. et al. *Biochem. J.* 151, 417–432 (1975).
16. Kluge, I., Gutteck-Amsler, U., Zollinger, M. & Do, K. Q. *J. Neurochem.* 69, 2599–2607 (1997).
17. Meyer, D. J., Kramer, H., Ozer, N., Coles, B. & Ketterer, B. *FEBS Lett.* 345, 177–180 (1994).
18. Huang, P. L., Dawson, T. M., Bredt, D. S., Snyder, S. H. & Fishman, M. C. *Cell* 75, 1273–1286 (1993).
19. Choi, Y. B. et al. *Nat. Neurosci.* 3, 15–21 (2000).
20. Beaumont, V. & Zucker, R. S. *Nat. Neurosci.* 3, 133–141 (2000).
21. Li, H. & Forstermann, U. *J. Pathol.* 190, 244–254 (2000).

22. Enikolopov, G., Banerji, J. & Kuzin, B. *Cell Death Differ.* 6, 956–963 (1999).
23. Inglis, F. M., Furia, F., Zuckerman, K. E., Strittmatter, S. M. & Kalb, R. G. *J. Neurosci.* 18, 10493–10501 (1998).
24. Kuzin, B. et al. *Curr. Biol.* 10, 459–462 (2000).
25. Nicotera, P., Leist, M. & Manzo, L. *Trends Pharmacol. Sci.* 20, 46–51 (1999).
26. Gross, W. L. et al. *Proc. Natl. Acad. Sci. U.S.A.* 93, 5604–5609 (1996).
27. Borgs, M. et al. *Hepatology* 23, 1564–1571 (1996).
28. Sato, T., Kamata, Y., Irifune, M. & Nishikawa, T. *Brain Res.* 704, 117–120 (1995).
29. Bonfoco, E. et al. *J. Neurochem.* 67, 2484–2493 (1996).
30. Andrade, F. H., Reid, M. B., Allen, D. G. & Westerblad, H. *J. Physiol. (Lond)* 509, 577–586 (1998).
31. Colledge, M. & Scott, J. D. *Trends Cell Biol.* 9, 216–221 (1999).
32. Christopherson, K. S., Hillier, B. J., Lim, W. A. & Bredt, D. S. *J. Biol. Chem.* 274, 27467–27473 (1999).
33. Jaffrey, S. R., Snowman, A. M., Eliasson, M. J., Cohen, N. A. & Snyder, S. H. *Neuron* 20, 115–124 (1998).
34. Stadtman, T. C. *Annu. Rev. Biochem.* 49, 93–110 (1980).
35. Wittschieben, B. O. et al. *Mol. Cell* 4, 123–128 (1999).

We claim:

1. A method for screening for potential drugs useful in modulating protein nitrosylation, comprising:
   contacting a test sample comprising at least one protein substrate with a test compound;
   treating the test sample with an alkylthiolating agent to block free thiol groups on the protein substrate;
   reducing nitrosothiol bonds on the protein substrate to form new free thiol groups;
   removing the alkylthiolating agent from the test sample;
   reacting the new free thiol groups on the protein substrate with a detectably tagged, activated mixed disulfide, thereby forming detectably tagged protein substrate, wherein the detectably tagged protein substrate indicates that the protein substrate in the test sample was nitrosylated;
   detecting the detectably tagged protein substrate; and
   comparing the amount of detectably tagged protein substrate in the test sample to an amount of detectably tagged protein substrate in a control sample similarly treated but not contacted with the test compound, wherein a test compound which increases or decreases the amount of detectably tagged protein substrate in the test sample relative to the control sample is identified as a modulator of protein nitrosylation.

2. The method of claim 1 wherein the alkylthiolating agent is methyl methanethiosulfonate (MMTS).

3. The method of claim 1 wherein ascorbate is added to the protein substrate during the step of reducing to accelerate the rate of reduction.

4. The method of claim 1 wherein the detectably tagged, activated mixed disulfide is biotinylated aromatic disulfide reagent N-[6-(biotinamido)hexyl]-3'-(2'-pyridyldithio)-propionamide (biotin-HPDP).

5. The method of claim 1 wherein the activated mixed disulfide comprises a radiolabel.

6. The method of claim 1 wherein the activated mixed disulfide comprises biotin.

7. The method of claim 1 wherein the activated mixed disulfide comprises dinitrophenol.

8. The method of claim 1 wherein the activated mixed disulfide comprises a peptide tag.

9. The method of claim 1 wherein the activated mixed disulfide comprises biotin and the biotin is detected using a biotin-specific antibody.

10. The method of claim 1 wherein the protein substrate is detected using an antibody specific for said protein substrate.

11. The method of claim 1 wherein the activated mixed disulfide comprises biotin and the biotin is detected using avidin.

12. The method of claim 1 wherein the activated mixed disulfide comprises biotin and the biotin is detected using streptavidin.

13. The method of claim 1 wherein the test sample is from brain tissue.

14. The method of claim 1 wherein the test sample is from blood vessels.

15. The method of claim 1 wherein the test sample is from macrophages.

16. The method of claim 1 wherein the test sample comprises eNOS.

17. The method of claim 1 wherein the test sample comprises nNOS.

18. The method of claim 1 wherein the test sample comprises iNOS.

19. The method of claim 1 wherein the protein substrate is glyceraldehyde-3 phosphate dehydrogenase.

20. The method of claim 1 wherein the protein substrate is creatine kinase.

21. The method of claim 1 wherein the protein substrate is hexokinase-1.

22. The method of claim 1 wherein the protein substrate is glycogen phosphorylase.

23. The method of claim 1 wherein the protein substrate is NR1 and/or NR2 subunits of NMDA glutamate receptor.

24. The method of claim 1 wherein the protein substrate is isoform 2 or 3 of hyperpolarization-activated cation channel (HAC).

25. The method of claim 1 wherein the protein substrate is $\alpha 1$ or $\alpha 2$ subunit of $Na^+/K^+$ ATPase.

26. The method of claim 1 wherein the protein substrate is neurofilament H-chain.

27. The method of claim 1 wherein the protein substrate is $\alpha$ or $\beta$ tubulin.

28. The method of claim 1 wherein the protein substrate is $\beta$ or $\gamma$ actin.

29. The method of claim 1 wherein the protein substrate is Retinoblastoma Gene Product, RB.

30. The method of claim 1 wherein the protein substrate is inducible heat shock protein 72.

31. The method of claim 1 wherein the protein substrate is collapsin response mediator protein 1, 2, and/or 4.

32. The method of claim 1 wherein the protein substrate is calbindin.

33. The method of any of claims 11–24 wherein an antibody specific for the protein substrate is used in the step of detecting.

34. The method of claim 1 wherein the step of removing involves subjecting the test sample to a spin column.

35. The method of claim 1 wherein the step of removing involves subjecting the test sample to acetone precipitation.

36. The method of claim 1 wherein SDS is added to the test sample to expose hidden thiol groups.

* * * * *